United States Patent [19]

Waller

[11] Patent Number: 4,987,248

[45] Date of Patent: Jan. 22, 1991

[54] ACID CATALYZED FORMATION OF CARBAMATES FROM OLEFINS

[75] Inventor: Francis J. Waller, Allentown, Pa.

[73] Assignee: E. I. du Pont de Nemours and Company, Wilmington, Del.

[21] Appl. No.: 388,401

[22] Filed: Aug. 2, 1989

[51] Int. Cl.$^5$ .......................................... C07C 261/00
[52] U.S. Cl. ................................. 560/157; 560/24; 560/29; 560/30; 560/31; 560/32; 560/33; 560/115; 560/160; 560/161; 560/163; 560/166
[58] Field of Search ............... 560/24, 115, 157, 29, 560/30, 31, 32, 33, 115, 160, 161, 163, 166

[56] References Cited

U.S. PATENT DOCUMENTS

| | | | |
|---|---|---|---|
| 3,520,916 | 7/1970 | Grakauskas | 260/468 |
| 4,176,215 | 11/1979 | Molnar et al. | 521/27 |
| 4,282,368 | 8/1981 | Merger et al. | 560/24 |
| 4,329,435 | 5/1982 | Kimoto et al. | 521/-8 |
| 4,330,654 | 5/1982 | Ezzell et al. | 526/243 |
| 4,439,616 | 3/1984 | Singh et al. | 560/25 |
| 4,476,316 | 10/1984 | Merger et al. | 560/24 |
| 4,552,974 | 11/1985 | Fukuoka et al. | 560/25 |
| 4,570,012 | 2/1986 | Singh et al. | 560/25 |
| 4,572,804 | 2/1986 | Mullins | 260/453 |
| 4,578,513 | 3/1986 | Singh et al. | 564/56 |
| 4,591,439 | 5/1986 | Grot | 210/638 |

FOREIGN PATENT DOCUMENTS

| | | | |
|---|---|---|---|
| 625748 | 12/1962 | Belgium. | |
| 291033 | 11/1988 | European Pat. Off. . | |
| 3233309 | 3/1984 | Fed. Rep. of Germany | 560/157 |
| 46-6043 | 2/1971 | Japan | 560/157 |
| 61-11942 | 4/1986 | Japan. | |

OTHER PUBLICATIONS

"Hackh's Chemical Dictionary", 4th ed., p. 131 (1969).

Primary Examiner—Michael L. Shippen

[57] ABSTRACT

An improved for preparing N-substituted carbamate comprising reaction of a selected olefin or alcohol with a carbamate in the presence of a catalyst comprising a blend of a perfluorinated sulfonic acid polymer and a perfluorinated polymer diluent in a substantially nonpolar reaction mixture.

26 Claims, No Drawings

ACID CATALYZED FORMATION OF CARBAMATES FROM OLEFINS

FIELD OF THE INVENTION

This invention relates to an improved process for the formation of N-substituted carbamates.

BACKGROUND OF THE INVENTION

Many N-substituted carbamates exhibit physiological activity and are useful as herbicides, insecticides or drugs. Other N-substituted carbamates can be used as intermediates in the phosgene-free synthesis of isocyanates which are widely used in the manufacture of fibers, coatings and other polymeric products.

The most commonly used routes to N-substituted carbamates are the reaction of alcohols with isocyanates and the reaction of alcohols with phosgene and substituted amines (Kuhr et al., "Carbamate Insecticides: Chemistry, Biochemistry, and Toxicology", CRC Press, Cleveland, Ohio, 1976). Although these methods provide the desired carbamates, they require the use of either potentially harmful isocyanates (e.g., methyl isocyanate) or highly toxic phosgene.

Belgian Pat. No. 625,748 discloses the preparation of carbamic acid esters with substitutents on the nitrogen atom by the addition of polymerizable olefins to carbamic acid esters having at least one hydrogen atom on the amine function in the presence of catalysts which react as acids. Specific acids which are disclosed include anhydrous mineral acids, such as hydrofluoric acid, hydrochloric acid, and hydrobromic acid, sulfuric, phosphoric and chlorosulfonic acid, as well as acidic anion exchangers, e.g., those based on polystyrene sulfonic acid and various Lewis acids. Preferably, boron trifluoride or its addition products are utilized.

U.S. Pat. No. 3,520,916 discloses the preparation of N-substituted-N-fluorocarbamates by acid catalyzed addition of an N-fluorocarbamate to an ethylenically unsaturated compound. Mineral acids such as concentrated sulfuric, hydrochloric and phosphoric acids, as well as Friedel-Crafts catalysts such as aluminum trichloride, ferric chloride, stannic chloride and boron trifluoride are disclosed as suitable acid catalysts.

U.S. Pat. No. 4,439,616 discloses the preparation of tertiary aralkyl urethane esters by the reaction of a carbamic acid ester of a lower aliphatic alcohol with an olefin at 40° C.–150° C. in the presence of an acid catalyst, such as sulfuric acid, toluene sulfonic acid, dodecyl benzene sulfonic acid, hydrocarbon sulfate esters, hydrochloric acid, boron trifluoride and other Lewis and Bronsted acids.

U.S. Pat. No. 4,570,012 discloses the preparation of tertiary aralkyl urethanes by reacting tertiary aralkyl diols with lower alkyl esters of carbamic acid in the presence of an acid catalyst to form N-substituted tertiary aralkyl carbamic acid esters. Suitable acid catalysts are sulfuric acid, toluene sulfonic acid, dodecylbenzene sulfonic acid, hydrocarbon sulfate esters, hydrogen chloride, boron trifluoride, and other Lewis and Bronsted acids.

U.S. Pat. No. 4,476,316 discloses the preparation of N-substituted carbamates by reacting a carbamate with an olefin in the presence of a cation exchanger containing sulfonic acid groups and of from 0.1 to 50 g of an alcohol per mole of carbamate starting material.

U.S. Pat. No. 4,578,513 discloses a process for making (phenylisopropyl)urea derivatives by the acid catalyzed addition of substituted ureas to isopropenyl aromatic compounds. The acid catalyst is chosen from concentrated sulfuric acid, a Lewis acid such as boron trifluoride, aluminum chloride or stannic chloride or a substituted sulfonic acid. Preferred acid catalysts include chlorosulfonic acid, p-toluenesulfonic acid, trifluoromethylsulfonic acid, boron trifluoride etherate and sulfuric acid.

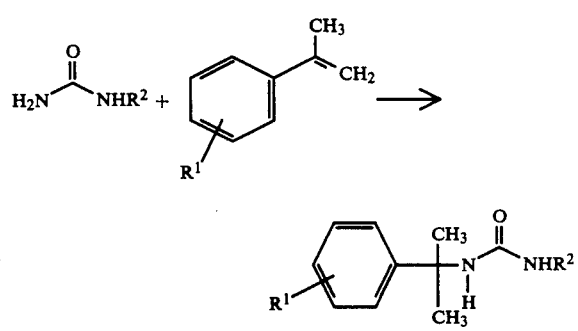

U.S. Pat. No. 4,572,804 (Col. 3, lines 35–40) discloses the preparation of geminal bis-carbamates by the acid catalyzed reaction of $\alpha, \beta$-unsaturated ethers with carbamates. This reaction was exemplified using p-toluene sulfonic acid. No other acids were disclosed for this reaction.

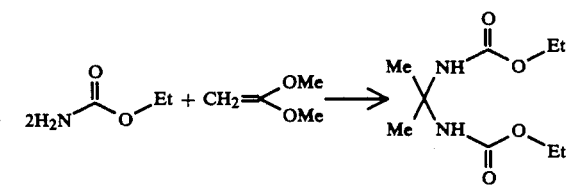

Fukuoka et al., Japanese Kokoku Patent Publication 61-11942, disclose a process for producing N-substituted carbamate esters, in which cyclohexane and a carbamate ester are reacted in the presence of a supported or unsupported heteropolyacid catalyst. The catalyst is a condensate of a multi-element oxyacid having dissimilar molecules arranged at the center, and has a condensation configuration with polyacid groups of tungsten, molybdenum, vanadium, niobium, etc., which share oxygen. The central elements include phosphorus, arsenic, silicon, germanium, titanium, cerium, thorium, boron, chromium, molybdenum, tungsten, selenium, tellurium, iron, cobalt, nickel manganese, iodine, etc.

U.S. Pat. No. 4,282,368 discloses a process for preparing p-substituted aromatic carbamic acid esters by reacting an aromatic carbamic acid ester with an olefin in the presence of an inorganic acid or a sulfonic acid.

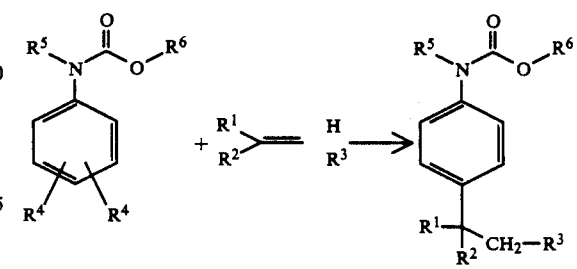

Preferred acid catalysts are organic cation exchangers containing sulfonic acid groups, including perfluorinated sulfonated polystyrene/divinylbenzene resins, perfluorinated, sulfonated crosslinked polystyrene resins and copolymers of tetrafluoroethylene and vinylsulfonic acid. This process provides only the aromatic alkylation product; N-alkylation is not disclosed.

U.S. Pat. No. 4,552,974 discloses the use of organic cation exchange resins having either fluoroalkyl sulfonic acid groups or fluoroalkyl carboxyl groups or both to produce diphenylmethane dicarbamate by reacting an N-phenylcarbamate with a methylenating agent (e.g., formaldehyde).

U.S. Pat. No. 4,176,215 discloses blends of fluorinated polymer which contains sulfonyl groups in ionizable form and a second fluorinated polymer which contains carboxylic acid functional groups. Blends are also disclosed which contain an additional inert polymer such as a copolymer of tetrafluoroethylene and perfluoropropylene.

European Patent Application 291,033 published Nov. 17, 1988, teaches use of perfluorinated acid ion exchange resins containing a group 8 metal in an oxidation state of at least +2 as catalysts for the isomerization of 3-pentenoic compounds to 4-pentenoic compounds. The resins include blends of fluorinated polymers containing sulfonic acid groups and fluorinated polymers containing carboxylic acid groups. Blends are also disclosed which contain copolymers such as tetrafluoroethylene.

U.S. Pat. No. 4,591,439 discloses a polymer blend comprising 75% perfluorocarbon polymer having sulfonyl exchange groups and an equivalent weight of 1100 and 25% copolymer of tetrafluoroethylene and hexafluoropropylene.

SUMMARY OF THE INVENTION

This invention provides an improved process for preparing N-substituted carbamates comprising reacting an olefin capable of undergoing cationic polymerization or an alcohol capable of forming a stable carbonium ion, with a carbamate, $H_2NC(O)OR$, in the presence of an acid catalyst, wherein the improvement is the use of an acid catalyst comprising a blend of a perfluorinated sulfonic acid polymer and a perfluorinated polymer diluent in a substantially nonpolar reaction mixture.

The improvement is characterized by increased activity of the catalyst blend over catalysts described in the art, where activity is defined as moles of product produced per mole of acid equivalent per unit time. This diluted catalyst blend is unexpectedly more active, and hence less expensive to use than a perfluorinated sulfonic acid polymer alone.

DETAILED DESCRIPTION OF THE INVENTION

The process of this invention provides N-substituted carbamates from the acid-catalyzed reaction of a suitable olefin or alcohol and a carbamate.

Suitable carbamate starting materials are non-basic esters of carbamic acid of the form $H_2NC(O)OR$, where R is $C_1$–$C_{10}$ straight-chained or branched alkyl or $C_7$–$C_{13}$ aralkyl, where R optionally contains halogen or ether substituents which are unreactive in the conditions of the acid-catalyzed reaction. Carbamic acid esters of polyalcohols, such as ethylene glycol, are also suitable. Preferred carbamates include methyl and ethyl carbamate.

Suitable olefins are those such as gem-disubstituted olefins and styrenes which are capable of forming relatively stable carbonium ions or those which can be polymerized by cationic polymerization. Suitable olefins generally form tertiary or benzylic carbonium ions upon protonation. Examples of suitable olefins include, but are not limited to, 2-methyl-2-butene, 2-methyl-1-butene, isobutylene, isoprene, styrene, α-methylstyrene, bis-isopropenylbenzene, methylene cyclohexane, and 2-methyl-1-pentene.

Suitable alcohols are those which can react with a Lewis or Bronsted acid to form a relatively stable carbonium ion, such as a tertiary or benzylic carbonium ion. Suitable alcohols include, but are not limited to, tertiary aliphatic alcohols such as t-butyl alcohol and t-amyl alcohol, and substituted derivatives thereof, and aryl-substituted alcohols such as benzyl alcohol and sec-phenethyl alcohol and substituted derivatives thereof.

Suitable acid catalysts are blends of at least one perfluorinated sulfonic acid polymer (i.e., a fluorinated polymer which has sulfonic acid functional groups) and at least one perfluorinated polymer diluent, where the combined weight ratio of acid polymer to diluent is between 99:1 and 1:2. Suitable perfluorinated sulfonic acid polymers are known in the art and include the Nafion ® polymers, which are catalysts for use in the manufacture of industrial chemicals and are available from E. I. du Pont de Nemours and Company. Suitable perfluorinated sulfonic acid polymers can also be made by the hydrolysis of sulfonyl-containing polymers such as those described in U.S. Pat. No. 4,330,654 and U.S. Pat. No. 4,329,435 which are hereby incorporated by reference. Nafion ® polymers are preferred.

Suitable perfluorinated polymer diluents for use in the catalyst blends are fluorinated polymers which contain functional groups which are inert under the reaction conditions. Suitable perfluorinated polymer diluents include, but are not limited to: polytetrafluoroethylene (PTFE, e.g., Teflon ®); copolymers of various combinations of tetrafluoroethylene, hexafluoropropylene, perfluoromethylvinyl ether and perfluorovinyl ether; and fluorinated polymers containing carboxylic acid functional groups.

The blends are not limited to two-component blends; multi-component blends are also possible. One example of a multi-component blend is a blend of two sulfonic acid-containing polymers with one diluent polymer; the two sulfonic acid-containing polymers could be different compositions, or be based on the same monomers but having different equivalent weights. Another example is a blend of one sulfonic acid-containing polymer with two diluent polymers. The two diluent polymers could be two polymers of different compositions or be based on the same monomer but having different equivalent weights. Preferably, the catalyst is a blend of perfluorinated sulfonic acid polymers and polytetrafluoroethylene in the ratio of 1:1 to 20:1, most preferably from 1:1 to 10:1.

The polymer blends can be prepared by coextruding the thermoplastic forms of the polymers as described in the art (e.g., U.S. Pat. No. 4,176,215). Powders, granules, or pellets of the individual polymers can first be mixed together. Such a mixture is then subjected to heat and pressure by various means, such as pressing, extruding in a screw extruder, or working on a roll mill or rubber mill. To assure formation of an intimate, uniform blend, the steps can be repeated two or more times. For example, pressed films can be flaked or cut into small pieces and repressed into film. Extruded polymer can be chopped into pellets as it is extruded, and then re-extruded. Powders for blending can be made by grinding in a mill or cold grinding in a freezer mill.

The sulfonyl groups are then converted to sulfonic acid groups. Such conversion is ordinarily accomplished by hydrolysis carried out with an aqueous solution of a mineral acid or alkali metal hydroxide. Base hydrolysis is preferred. Use of hot solution, near the boiling point of the solution, is preferred for rapid hydrolysis. It can also be of advantage to include a water-miscible organic compound such as dimethylsulfoxide in the hydrolysis bath.

The process of this invention is generally performed by charging the reaction vessel with the olefin or alcohol, the carbamate, the acid catalyst and, optionally, solvent, and heating the reaction mixture. Alternatively, the catalyst can be added after the olefin or alcohol, the carbamate and solvent (if desired) have been charged in the reaction vessel and heated. When the reaction is complete, the N-substituted carbamate product is obtained by filtering off the catalyst and isolating the carbamate from the filtrate by distillation or crystallization, as appropriate.

The amounts of reagents are arbitrary, but preferably the ratio of olefin or alcohol to carbamate is 1:5 to 10:1. More preferably, the ratio of olefin or alcohol to carbamate is 1:1 to 2:1.

The ratio of carbamate to sulfonic acid catalyst group is 10:1 to 1000:1, preferably 20:1 to 200:1. If the only acidic functional groups are the catalytically active sulfonic acid groups, the equivalent weight of the catalyst blend can be determined by titration of the acid groups with standardized base (e.g., NaOH) using an indicator such as phenolphthalein. If other acidic groups, e.g., carboxylic acid groups, are present, titration will give the equivalent weight for the combined acid groups. The ratio of sulfonic to carboxylic acid groups can then be determined by treating two separate samples of the catalyst blend with aqueous KCl and aqueous $K_2CO_3$ and determining the amount of K incorporated in each sample by elemental analysis. KCl replaces only the sulfonic acid protons with K, whereas $K_2CO_3$ replaces both the sulfonic and carboxylic acid protons with K.

Suitable solvents for the reaction of this invention are hydrocarbon (e.g., petroleum ether, cyclohexane), halocarbon (e.g., methylene chloride, carbon tetrachloride), aromatic (benzene, toluene, xylene) or haloaromatic (e.g., chlorobenzene) solvents. Alternatively, the olefin, alcohol or carbamate can serve as the solvent. The reaction mixture is substantially nonpolar. As polarity increases, the activity of the catalyst blend diminishes. Thus, a reaction mixture that is largely, but not necessarily wholly, nonpolar is desired. Use of the catalyst blend, even in a polar reaction mixture, is advantageous because the catalyst blend of a perfluorinated sulfonic acid polymer and perfluorinated polymer diluent is less expensive to use than a perfluorinated sulfonic acid polymer alone. However, to maximize the activity of the catalyst blend, a substantially nonpolar reaction mixture is required. Preferably the reaction mixture is nonpolar.

The reaction can be conducted at atmospheric or elevated pressures, depending on the boiling point of the olefin or alcohol and solvent. The reaction temperature is a function of the reactivity of the olefin or alcohol, but is generally between 0° C. and 200° C., preferably 20° C. to 150° C. The reaction time is 5 minutes to 24 hours.

The process of this invention is further illustrated by the following Examples and Comparative Experiments. In particular, it should be noted that the catalyst blends of this process give substantially and unexpectedly higher turnover rates (moles of N-substituted carbamate per mole of ion-exchange capacity) than acid catalysts of the prior art, or even of the components of the catalyst blend. "Ion exchange capacity" is defined as 1000 divided by the equivalent weight of the polymer. "Mequiv" (millequivalents) reflects the total ion exchange capacity of the catalysts.

EXAMPLES

Examples 1-11 and

Comparative Experiments A-C

These examples illustrate that blends of perfluorinated sulfonic acid polymers and perfluorinated diluent polymers give higher turnover rates than perfluorinated sulfonic acid polymers or perfluorinated carboxylic acid polymers alone.

A round-bottom flask was charged with 2-methyl-2-butene (4.6 g, 65.7 mmol), methyl carbamate (2.5 g, 33.3 mmol), chlorobenzene (1.0 g, standard), and benzene (30.0 mL). After heating this mixture to reflux (68-70° C.), catalyst (0.6, 0.9 or 1.2 g), was added. Samples were withdrawn at 30 minute intervals and analyzed by gas chromatography (GC.). GC. analysis was performed on either a ⅛" (3 mm) diameter, 10' (3.05 m) column packed with SE-30ABS or a 50' (15.3 m) cross-linked methyl silicone fused silica capillary column programmed for 60° C. to 200° C. at 8° C. min$^{-1}$. The reactions were usually stopped before 50% of the methyl carbamate reacted to form product. Results are presented in Table 1.

TABLE 1

| | Catalyst Activity vs. Blend Composition[a] | | | |
|---|---|---|---|---|
| Ex. | Catalyst Composition | Catalyst (g, % SAP[b]) | Amount (mequiv.) | TOR[f] |
| 1 | SAP/CAP[c] | 0.6, 90 | 0.456 | 0.14 |
| 2 | SAP/CAP | 0.9, 90 | 0.684 | 0.14 |
| 3 | SAP/CAP | 0.6, 79 | 0.417 | 0.13 |
| 4 | SAP/CAP | 0.6, 75 | 0.39 | 0.06 |
| 5 | SAP/CAP | 0.9, 75 | 0.585 | 0.09 |
| 6 | SAP/CAP | 0.6, 66.6 | 0.384 | 0.13 |
| 7 | SAP/CAP | 0.9, 66.6 | 0.576 | 0.16 |
| 8 | SAP/CAP | 0.6, 50 | 0.381 | 0.17 |
| 9 | SAP/CAP | 0.9, 50 | 0.571 | 0.20 |
| 10 | SAP/FEP[d] | 0.6, 66[c] | 0.312 | 0.14 |
| 11 | SAP/TFE[e] | 0.6, 62[d] | 0.294 | 0.26 |
| A | CAP | 1.2, 0 | 1.143 | N.R. |
| B | SAP | 0.6, 100 | 0.477 | 0.047 |
| C | SAP | 0.9, 100 | 0.716 | 0.049 |

[a]Blends of perfluorinated sulfonic acid polymer and perfluorinated diluent polymer
[b]SAP = Perfluorinated sulfonic acid polymer
[c]CAP = Perfluorinated carboxylic acid polymer
[d]SAP/Teflon FEP ® blend, 66/34
[e]SAP/Teflon ® blend, 62/38
[f]TOR = mmol of product per mequiv. of total ion exchange capacity per minute

EXAMPLES 12-13 and

Comparative Experiments D-K

These examples and comparative experiments show that the blends of perfluorinated sulfonic acid polymers and perfluorinated carboxylic acid polymers give higher turnover rates than other strong acid catalysts.

A round-bottom flask was charged with olefin, carbamate, chlorobenzene (1.0 g, standard) and benzene (30 mL). After heating the resulting mixture to reflux, catalyst was added to the solution. Samples were withdrawn periodically and analyzed by GC. The results are presented in Table 2.

TABLE 2

Catalyst Activity of Blends v. Other Strong Acid Catalysts

| Ex. | Catalyst SAP/CAP[c] | Amount (mequiv.) | TOR[d] | Olefin |
|---|---|---|---|---|
| 12 | Blend[a] 79/21 | 0.21 | 2.6 | 2-Me-1-butene |
| 13 | Blend[b] 79/21 | 0.53 | 0.2 | 2-Me-2-butene |
| D | SAP[a] 100% | 0.6 | 0.61 | 2-Me-1-butene |
| E | SAP[b] 100% | 0.48 | 0.05 | 2-Me-2-butene |
| F | Amberlyst 15 ® | 2.82 | 0.095 | 2-Me-1-butene |
| G | Amberlyst 15 ® | 2.82 | 0.016 | 2-Me-2-butene |
| H | $CF_3CO_2H$ | 2.63 | N.R. | 2-Me-2-butene |
| I | Amberlite | 6.98 | N.R. | 2-Me-2-butene |
| J | $H_2SO_4$ | 3.06 | 0.08 (stops after 20 min.) | 2-Me-1-butene |
| K | p-tolyl-sulfonic acid | 2.32 | 0.006 (stops after 50 min.) | 2-Me-1-butene |

[a]60–100 mesh
[b]10–35 mesh
[c]SAP = perfluorinated sulfonic acid polymer   CAP = perfluorinated carboxylic acid polymer
[d]TOR = mmol of product per mequiv. of total ion exchange capacity per minute

EXAMPLES 14–27

These examples illustrate the use of blends of perfluorinated sulfonic acid polymers (SAP) and perfluorinated carboxylic acid polymers (CAP) to prepare a variety of N-substituted carbamates.

For the isobutylene reactions, a 90 cc Fischer Porter (F-P) tube was charged with isobutylene (268 mmol), $H_2NCO_2Me$ (66.7 mmol), catalyst (SAP/CAP = 79/21, 60–100 mesh), methylene chloride or benzene (8 mL), and chlorobenzene (1.0 g, standard). The F-P tube was heated to 80° C. for 30 minutes, and the reaction mixture analyzed by gas chromatography. The results are presented in Table 3.

For the other reactions, a round-bottom flask was charged with olefin or alcohol, carbamate, catalyst (SAP/CAP = 79/21, 60–100 mesh), chlorobenzene (1.0 g, standard) and benzene (30 mL). After heating the resulting mixture to reflux, catalyst was added to the solution. Samples were withdrawn periodically and analyzed by 9as chromatography. The results are presented in Table 3.

TABLE 3

Perpration of N-Substituted Carbamates

| Ex. | Catalyst (mequiv) | Olefin/Alcohol (mmol) | Carbamate (min) | Time | Yield % |
|---|---|---|---|---|---|
| 14 | 0.42 | 2-Me-1-butene 60.0 | $H_2NCO_2Me$ 30.7 | 50 | 91.3 |
| 15 | 2.43 | 2-Me-1-butene 60.0 | $H_2NCO_2Et$ 28.1 | 40 | 91.1 |
| 16 | 2.43 | 2-Me-2-butene 60.0 | $H_2NCO_2Me$ 30.7 | 60 | 100 |
| 17 | 2.43 | 2-Me-2-butene 60.0 | $H_2NCO_2Et$ 28.1 | 60 | 88.7 |
| 18 | 1.25 | Isobutylene 268 | $H_2NCO_2Me$ 66.7 | 30 | 100 |
| 19 | 0.42 | Isobutylene[a] 268 | $H_2NCO_2Me$ 66.7 | 30 | 27.9 |
| 20 | 1.25[b] | Isobutylene 268 | $H_2NCO_2Me$ 66.7 | 30 | 73.9 |
| 21 | 0.42 | α-Me-styrene 58.5 | $H_2NCO_2Et$ 25.8 | 10 | 83 |
| 22 | 0.42 | methylene-cyclohexane, 52.1 | $H_2NCO_2Me$ 30.7 | 90 | 45.3 |
| 23 | 0.42 | 2-Me-1-pentene 29.8 | $H_2NCO_2Et$ 14.6 | 150 | 46.3 |
| 24 | 0.83[b] | t-butanol 108 | $H_2NCO_2Me$ 40 | 60 | 24.8 |
| 25 | 0.42 | t-amyl alcohol 60.2 | $H_2NCO_2Me$ 30.7 | 100 | 13.5 |
| 26 | 0.42[b] | sec-phenethyl alcohol, 33 | $H_2NCO_2Me$ 33 | 120 | 64.5 |
| 27 | 0.69[b] | benzyl alcohol 26.9 | $H_2NCO_2Me$ 26.7 | 120 | 2.3[c] |

[a]Benzene solvent
[b]35–60 mesh
[c]F-P tube; 10 mL benzene solvent

What is claimed is:

1. An improved process for the preparation of N-substituted carbamic acid esters by reacting a carbamic acid ester reactant having two hydrogen substituents on the nitrogen atom with an olefin capable of undergoing cationic polymerization or an alcohol capable of forming a stable carbonium ion in the presence of an acid catalyst wherein the improvement comprises the use of an acid catalyst which is a blend of a perfluorinated sulfonic acid polymer and a perfluorinated polymer diluent in a substantially nonpolar reaction mixture.

2. The process of claim 1 wherein the diluent is selected from polytetrafluoroethylene; copolymers of two or more of tetrafluoroethylene, hexafluoropropylene, perfluoromethylvinyl ether and perfluorovinyl ether; and perfluorinated polymers containing carboxylic acid functional groups.

3. The process of claim 2 wherein the catalyst is a blend of perfluorinated sulfonic acid polymers and polytetrafluoroethylene in a ratio of from about 1:2 to about 20:1.

4. The process of claim 3 wherein the ratio is from about 1:1 to about 10:1.

5. The process of claim 4 wherein the ratio is about 1.6:1.

6. The process of claim 2 wherein the catalyst is a blend of perfluorinated sulfonic acid polymer and perfluorinated carboxylic acid polymer.

7. The process of claim 6 wherein the ratio of sulfonic acid polymer to carboxylic acid polymer is from about 1:1 to about 10:1.

8. The process of claim 7 wherein the ratio of sulfonic acid polymer to carboxylic acid polymer is about 3.8:1.

9. The process of claim 2 wherein the ratio of olefin or alcohol to carbamate is from about 1:5 to about 10:1.

10. The process of claim 9 wherein the ratio is about 1:1 to about 2:1.

11. The process of claim 2 wherein the ratio of carbamic acid ester reactant to catalyst is from about 10:1 to about 1000:1.

12. The process of claim 11 wherein the ratio is from about 20:1 to about 200:1.

13. The process of claim 2 wherein the reaction mixture contains a solvent selected from a hydrocarbon or halogen substituted hydrocarbon, including aromatic hydrocarbon or halogen substituted aromatic hydrocarbon compound.

14. The process of claim 13 wherein the solvent is a mixture of chlorobenzene and benzene.

15. The process of claim 13 wherein the solvent is benzene.

16. The process of claim 2 conducted at a temperature of from about 0° C. to 200° C.

17. The process of claim 16 wherein the temperature is from about 20° C. to about 150° C.

18. The process of claim 2 wherein the olefin is 2-methyl-2-butene, 2-methyl-1-butene, isobutylene, isoprene, styrene, α-methylstyrene, bis-isopropenylbenzene, methylene cyclohexane, or 2-methyl-1-pentene.

19. The process of claim 4 or 7 wherein the olefin is 2-methyl-2-butene.

20. The process of claim 7 wherein the olefin is 2-methyl-1-butene.

21. The process of claim 2 wherein the alcohol is a tertiary aliphatic alcohol, aryl-substituted alcohol, or polyalcohol.

22. The process of claim 7 wherein the alcohol is t-butanol, t-amyl alcohol, sec-phenethyl alcohol, or benzyl alcohol.

23. The process of claim 2 wherein the carbamic acid ester reactant is $H_2NC(O)OR$ wherein R is $C_1$–$C_{10}$ straight or branched chain alkyl, $C_1$–$C_{10}$ straight or branched alkyl substituted with halogen or ether, $C_7$–$C_{13}$ aralkyl, or $C_7$–$C_{13}$ aralkyl substituted with halogen or ether.

24. The process of claim 23 wherein R contains unreactive halogen or ether substituents.

25. The process of claim 4 or 7 wherein the carbamic acid ester reactant is methyl carbamate.

26. The process of claim 4 or 7 wherein the carbamic acid ester reactant is ethyl carbamate.

* * * * *